United States Patent [19]

Kelly

[11] 3,993,686

[45] Nov. 23, 1976

[54] PHENYL SUBSTITUTED PROSTAGLANDINS-C-TYPE ANALOGS

[75] Inventor: Robert C. Kelly, Kalamazoo, Mich.

[73] Assignee: The Upjohn Company, Kalamazoo, Mich.

[22] Filed: Nov. 12, 1973

[21] Appl. No.: 415,050

[52] U.S. Cl. .................. 260/473 A; 260/240 R; 260/343.3 R; 260/345.7; 260/345.8; 260/347.3; 260/347.4; 260/347.5; 260/448.2 Q; 260/448.2 R; 260/468 D; 260/514 D; 260/520 B; 424/305; 424/308

[51] Int. Cl.$^2$......................................... C07C 69/76

[58] Field of Search....................... 260/473 A, 520

[56] References Cited

UNITED STATES PATENTS 3,678,092  7/1972  Finch .............................. 260/473 A

FOREIGN PATENTS OR APPLICATIONS 2,154,301  5/1972  Germany
2,314,519  10/1973  Germany

OTHER PUBLICATIONS

Jones, Brit. J. Pharmacol. 45 144p–145p (1972).
Jones, Biochem. Biophys. Acta. 280 (1972) 588–601.

*Primary Examiner*—Paul J. Killos
*Attorney, Agent, or Firm*—Robert A. Armitage; Ward F. Nixon

[57] ABSTRACT

Process for the total synthesis of 11,12-unsaturated prostaglandin compounds, i.e., prostaglandin $C_2$-type compounds and analogs, and to certain novel compounds and intermediates produced thereby. The compounds produced by said process are useful as vasodepressors and antisecretory agents, and in managing cases of renal disfunction.

12 Claims, No Drawings

PHENYL SUBSTITUTED PROSTAGLANDINS-C-TYPE ANALOGS

BACKGROUND

Certain prostaglandin type C compounds and processes for their preparation have been disclosed in the literature. $PGC_2$ is disclosed by R. L. Jones, Brit. J. Pharmacol. 45, 144P – 145P (1972) and Biochim. Biophys. Acta, 280 (1972) 588–601, wherein $PGC_2$ is reported to have 3-fold greater depressor activity than its precursors, the corresponding $PGA_2$ compound, and 50-fold greater activity than the corresponding $PGB_2$ compound. Crabbé et al., Tetrahedron Letters No. 32, pp 3021–3022 (1973) have reported the synthesis of the corresponding 9α-hydroxy $PGC_2$ (9α,11α-dihydroxyprosta-5-cis-11,13-trans-trienoic acid) and certain of the intermediates disclosed herein.

Each of the above-mentioned known prostaglandins is a derivative of prostanoic acid which has the following structure and atom numbering:

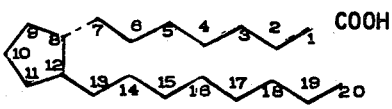

See, for example, Bergstrom et al., Pharmacol, Rev. 20, 1 (1968), and references cited therein. A systematic name for prostanoic acid is 7-[(2β-octyl)-cyclopent-1α-yl]-heptanoic acid.

$PGA_1$ has the following structure:

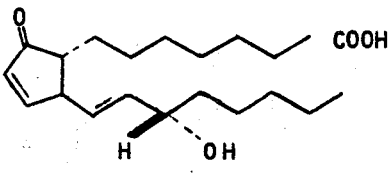

$PGA_2$ has the following structure:

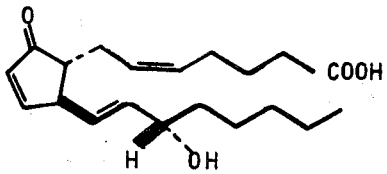

$PGB_1$ has the following structure:

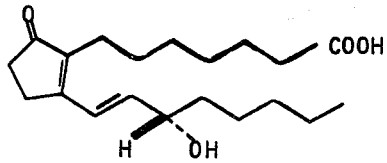

$PGB_2$ has the following structure:

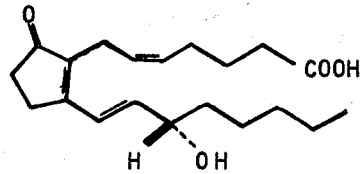

$PGC_1$ has the following structure:

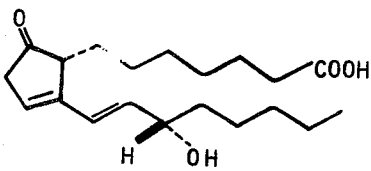

$PGC_2$ has the following structure:

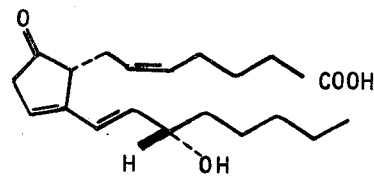

In the above formulas, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 when drawn with a broken line as in the above formulas and some of those which follow hereinafter is in the S configuration, although α is preferred as a designation for this configuration. The side chain hydroxy at C-15 when drawn with a heavy solid line as in some of the formulas which follow hereinafter is in the R configuration. This configuration is also known as epi, although β is preferred as a designation. See Nature, 212, 38 (1966), Hamberg, European J. Biochem, 6, 147 (1968), and Weinheimer et al., Tetrahedron letters 49, 5185 (1969), and references cited in those, for discussions of the stereochemistry of these prostaglandins.

Molecules of the known prostaglandins each have several centers of asymmetry, and can exist in racemic (optically inactive) form and in either of the two enantiomeric (optically active) forms, i.e., the dextrorotatory and levorotatory forms. As drawn, the above formulas represent optically active compounds each with the same absolute configuration as optically active prostaglandin $E_1$ ($PGE_1$) obtained from certain mammalian tissues, for example, sheep vesicular glands or human seminal plasma. See, for example, Bergstrom et al., J. Biol. Chem, 238, 3555 (1963), Horton, Experientia, 21, 113 (1965), Bergstrom et al., Pharmacol. Rev. 20, 1 (1968), and references cited in those. The mirror image of each of above formulas represents the other enantiomer of that prostaglandin, The racemic form of a prostaglandin contains equal numbers of both enantiomeric molecules, and one of the above formulas and the mirror image of that formula is needed to represent correctly the corresponding racemic prostaglandin. For convenience hereinafter, use of the term $PGC_2$ and the like, will mean the optically active form of that prostaglandin with the same absolute configuration as $PGE_1$ obtained from mammalian tissues. When reference to the racemic form of one of those prostaglandins is intended, the word "racemic" of "dl" will preceed the prostaglandin name.

DESCRIPTION OF THE INVENTION

This invention relates to novel processes for total synthesis of 11,12-unsaturated prostaglandin compounds, i.e. prostaglandin type C compounds and to intermediates and to certain novel prostaglandin type C compounds, produced thereby. More specifically, this invention is concerned with a process for the total synthesis of optically active and racemic organic compounds of the formula:

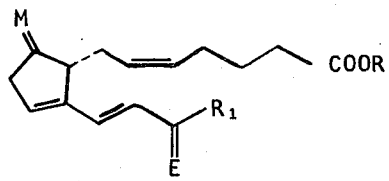

wherein M is

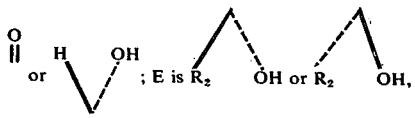

in which $R_2$ is hydrogen or lower-alkyl of 1 to 4 carbon atoms, inclusive, R is hydrogen, alkyl of 1 to 2 carbon atoms, inclusive, cycloalkyl of 3 to 10 carbon atoms, inclusive, phenyl, aralkyl of 7 to 12 carbon atoms, inclusive, phenyl substituted with 1 to 3 chlorine atoms, inclusive, phenyl substituted with lower-alkyl of 1 to 4 carbon atoms, inclusive; and $R_1$ is

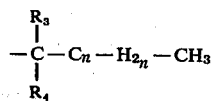

or

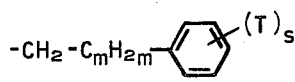

in which $R_3$ and $R_4$ are each hydrogen, fluoro or lower-alkyl of 1 to 4 carbon atoms, inclusive, with the proviso that $R_3$ is fluoro only when $R_4$ is hydrogen or fluoro; $-C_nH_{2n}-$ is straight chain alkylene of 1 to 5 carbon atoms, inclusive; $-C_mH_{2m}-$ is a valence bond or alkylene of 1 to 9 carbon atoms, inclusive, with 1 to 6 carbon atoms, inclusive, in a chain between $-CH_2-$ and the ring; and T is lower-alkyl of 1 to 4, carbon atoms, inclusive, fluoro, chloro, trifluoromethyl, or $-OR_2$, in which $R_2$ is hydrogen or alkyl of 1 4 carbon atoms, inclusive, and s is 0 to 3, inclusive, with the proviso that not more than two T's are other than alkyl. Preferred compounds with a phenyl terminated side chain are those wherein $-C_mH_{2m}-$ is alkylene of 1 carbon atom, (methylene), and those wherein s is 0 and those wherein s is 1 and T is p-chloro.

Novel compounds which are included within the scope of this invention are racemic and optically active compounds of the formulas:

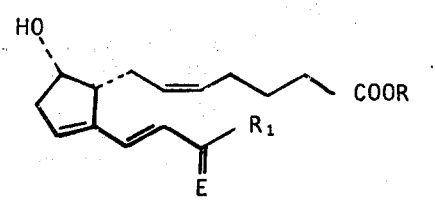

Ia

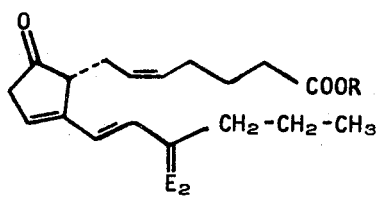

Ib

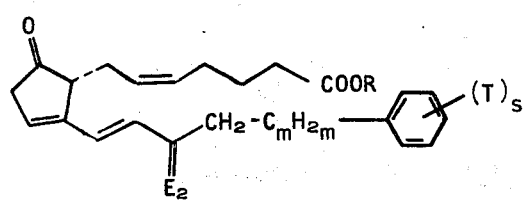

Ic and

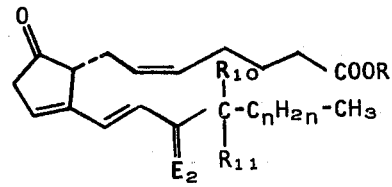

Id

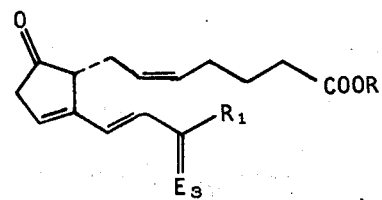

Ie wherein E, R, R₁, —C$_n$H$_{2n}$—; —C$_m$H$_{2m}$—, T and s have the meanings given, above; R$_{10}$ is hydrogen, fluoro or lower-alkyl of 1 to 4 carbon atoms, inclusive and R$_{11}$ is fluoro or lower-alkyl of 1 to 4 carbon atoms, inclusive and R$_{11}$ is fluoro or lower-alkyl of 1 to 4 carbon atoms, inclusive,

in which R$_{12}$ in lower-alkyl of 1 to 4 carbon atoms inclusive, and the pharmacologically acceptable salts of the compounds of formulae I*a*, I*b*, I*c*, I*d*, and I*e* wherein R is hydrogen. The compounds of formulas I*a*, I*b*, I*c*, I*d*, and I*e* fall within the scope of formula I, above, and are useful for the same purposes as the compounds of formula I.

In this application the term lower-alkyl means an alkyl radical of 1 to 4 carbon atoms such as methyl, ethyl, propyl, butyl and isomeric forms thereof, of these methyl and ethyl are preferred and methyl is especially advantageous.

The novel PGC$_2$ compounds of formula I are useful as hypotensive agents to reduce blood pressure in mammals, including man, especially in cases of essential hypertension. For this purpose and with particular regard to humans, the compounds are administered by intravenous infusion at the rate about 0.01 to about 50 μg. per kg. of body weight per minute, preferably at a rate about 0.1 to 5 μg. per kg. per minute, or in single or multiple intravenous doses of about 25 to 500 μg. per kg. of body weight total per day, the exact dose depending on the particular novel PGC$_2$ compound used, on the age and weight of the subject, and on the severity of the hypertensive condition. The doses given herein are especially suitable for use of PGC$_2$ itself or a salt thereof, and somewhat higher dose levels may be needed for some of the PGC$_2$ esters and some of the other novel PGC$_2$ analogs of this invention. An appropriate dose range is readily determined for these other novel compounds by comparing the depressor activity of the particular compound with that of PGC$_2$ in laboratory animals, for example, by the procedures described in Weeks et al. or Horton et al., above cited.

The novel PGC$_2$ compounds of formula I increase the flow of blood in the mammalian kidney, thereby increasing volume and electrolyte content of the urine. For that reason, these novel PGC$_2$ compounds are useful in managing cases of renal disfunction, especially those involving blockage of the renal vacular bed. Illustratively, the PGC$_2$ compounds are useful to alleviate and correct cases of edema resulting, for example, from massive surface burns, and in the management of shock. For these purposes and with particular regard to humans, compounds are preferably first administered by intravenous injection at a dose in the range 10 to 1000 μg. per kg. of body weight, preferably in the range 100 to 500 μg. per kg. of body weight, or by intravenous infusion at a dose in the range 0.1 to 20 μg. per kg. of body weight per minute until the desired effect is obtained. Subsequent maintenance doses are given by intravenous injection or infusion, or intramuscular or subcutaneous injection in the total range 0.05 to 2 mg. per kg. of body weight per day. The doses given here are especially suitable for PGC$_2$.

The novel PGC$_2$ compounds of formula I are useful in mammals, including man and certain useful animals, e.g., dogs and pigs, to reduce and control excessive gastric secretion, thereby reducing or avoiding gastrointestinal and duodenal ulcer formation, and accelerating the healing of such ulcers already present in the gastrointestinal and duodenal tracts. For this purpose, the compounds are injected or infused intravenously, subcutaneously, or intramuscularly in an infusion dose range about 0.1 μg. to about 500 μg. per kg. of body weight per minute, preferably in the range 1 to 50 μg. per kg. per minute, or in a total daily dose by injection or infusion in the range about 0.1 to about 20 mg. per kg. of body weight per day, or are administered orally in the range 0.1 to 50 mg. per kg. of body weight per day, the exact dose depending on the age, weight, and condition of the patient or animal, and on the frequency and route of administration.

The compounds of formula I are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The compounds of formula I are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-natural labor has not started, or 12 to 60 hours after the membranes have ruptured and natural labor has not yet started. An alternative route of administration is oral.

The compounds of formula I are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, the compounds for example, are administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

The $PGC_2$ compounds of formula I are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The compounds of formula I are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the forms of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and or the frequency and route of administration. For the above use these prostaglandins can be combined advantageously with other antiasthmatic agents, such as, sympathomimetics (isoproterenol, phenylephrine, ephedrine, etc.); xanthine derivatives (theophylline and aminophyllin); and corticosteroids (ACTH and prednisolone). Regarding use of these compounds for for these purposes, see South African Pat. No. 68/1055.

For all of the above purposes, the novel formula I compounds are used in free acid form, as esters, or in pharmacologically acceptable salt form.

When the ester form is used, any ester within the range of the above definition of R is used. With ragard to said definition, examples of alkyl of one to 12 carbon atoms, inclusive, are methyl, ethyl, propyl, butyl, pentyl, hexyl, heptyl, octyl, nonyl, decyl, undecyl, and dodecyl, and isomeric forms thereof, for example isopropyl, sec. butyl, and 2-ethylhexyl. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Of these esters within the scope of R, it is preferred that the ester be alkyl of one to 4 carbon atoms, inclusive. Of those alkyl, methyl is especially preferred for optimum absorption by the animal body. The straight-chain octyl, nonyl, decyl, undecyl, and dodecyl esters are also especially preferred for prolonged activity in the animal body.

Pharmacologically acceptable salts of these novel $PGC_2$ compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like, aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of formula I are preferred. For example, it is preferred that the hydroxyl at C-15 be in the alpha configuration. It is also preferred that any branching of the $R_1$ group in the methyl-terminated chain be at C-16. Preferred compounds are for example, $PGC_2$, $PGC_2$ methyl ester, 15(S)-15-methyl-$PGC_2$ methyl ester, 16, 16-dimethyl-$PGC_2$ methyl ester, 16-fluoro-$PGC_2$ methyl ester, and the like.

As discussed above, the novel compounds of formula I are administered in various ways, e.g., intravenously, intramuscularly, or subcutaneously. For intravenous injection or infusion, sterile aqueous isotonic solutions are preferred. For subcutaneous or intramuscular injection, sterile solutions or suspensions in aqueous or non-aqueous media are used.

It is important when preparing the various novel $PGC_2$ compounds of this invention as described hereinafter and in storing, formulating, dispensing, and administrating them, that they not be allowed contact with base and that solutions, especially aqueous solutions, containing them be maintained at a pH less than about 7, preferably in the pH range about 6 to 6.5. A basic environment results in a substantial and usually rapid decrease in biological activity of the $PGC_2$ compound. This loss in activity occurs substantially more slowly in a neutral or mildly acidic medium. If the storage or dispensing container is made of glass, the container should be washed with acid, e.g., acetic acid, before use. Although salts of the $PGC_2$ compounds are suitably stable in solid form or in the absence of water or other polar solvents, solutions of the salt form should be buffered so that the pH of the solution is below about 7. The esters of these $PGC_2$ compounds, especially the methyl esters, are somewhat more stable than the free acid or salt forms, and for that reason, these esters, especially the alkyl esters of one to 4 carbon atoms, inclusive, in the alkyl portion, and more especially the methyl and ethyl esters, represent preferred embodiments of this invention.

The process for the total synthesis of the compounds of formula I (including $1a - 1e$) is illustratively represented by the following sequence of formulas:

Chart I

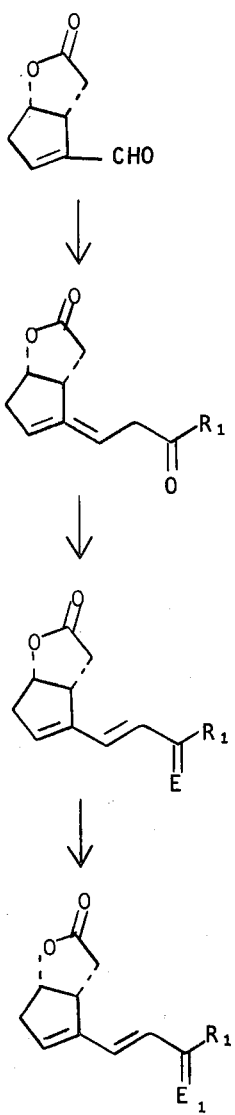

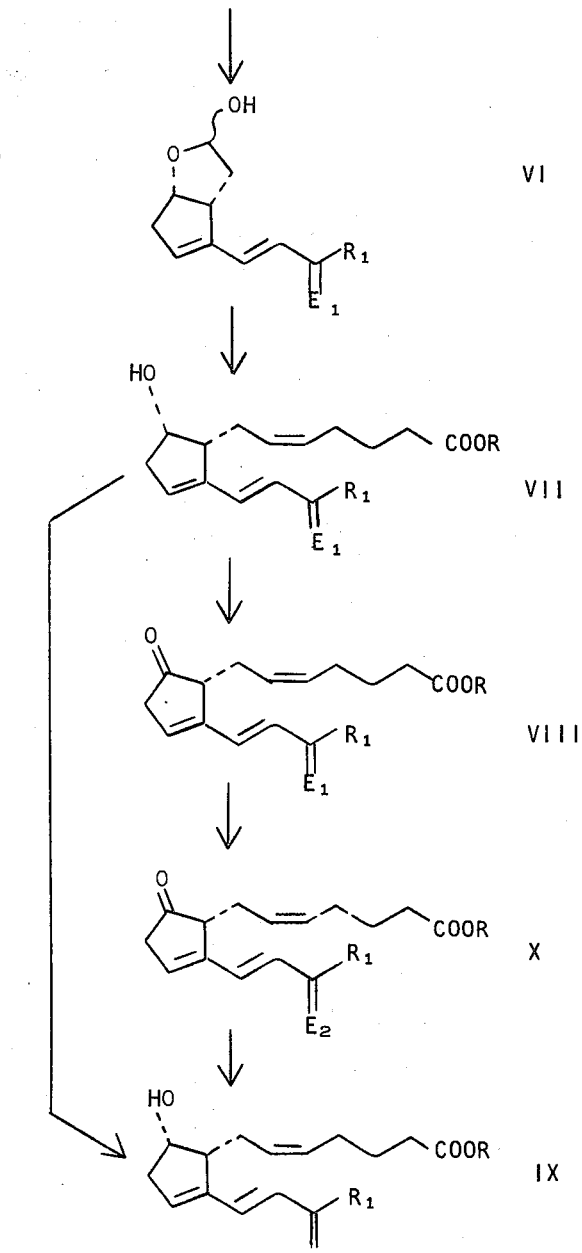

wherein R, $R_1$, E, and $E_2$ have the meanings previously given; and $E_1$ is

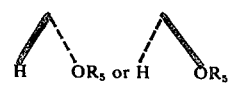

and $R_5$ is (a) tetrahydropyranyl, (b) tetrahydrofuranyl, (c) a group of the formula:

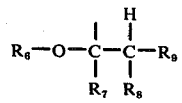

in which $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive; in which $R_7$ and $R_8$ are each hydrogen, lower-alkyl of one to 4 carbon atoms, inclusive, phenyl or phenyl substituted with 1, 2, or 3 lower-alkyl groups of one to 4 carbon atoms inclusive, or, when $R_7$ and $R_8$ are taken together, $-(CH_2)_a-$ or $-(CH_2)_b-O-(CH_2)_c-$ in which $a$ is 3, 4, or 5, $b$ is 1, 2, or 3, and $c$ is 1, 2, or 3 with the proviso that $b$ plus $c$ is 2, 3, or 4; and $R_9$ is hydrogen or phenyl, or $(d)$ silyl of the formula $-Si(G)_3$ wherein G is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, and wherein R, $R_1$, E and $E_3$ have the meanings previously given.

The optically active or racemic starting material of formula II is prepared in accordance with Chart III and Preparation I, contained herein:

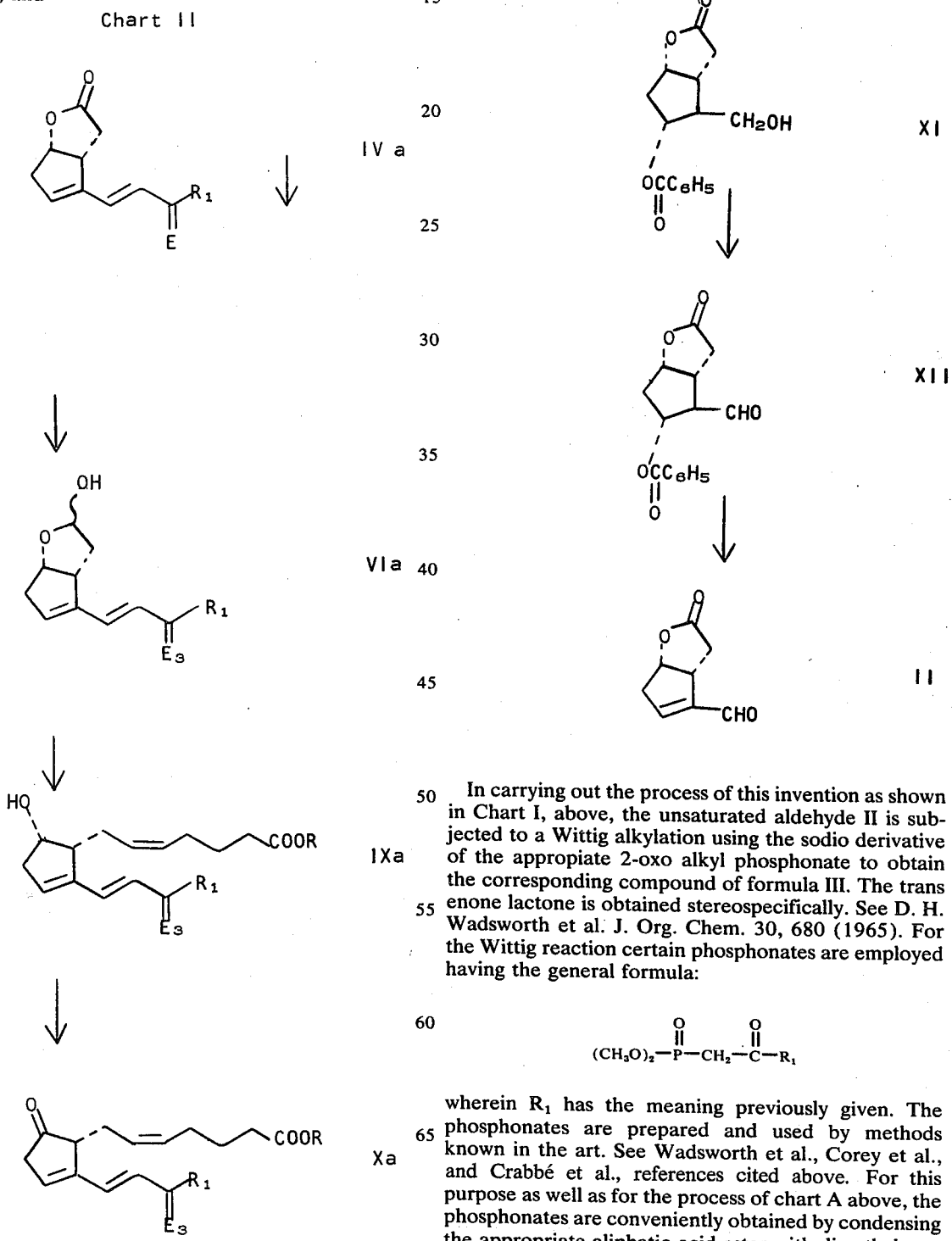

In carrying out the process of this invention as shown in Chart I, above, the unsaturated aldehyde II is subjected to a Wittig alkylation using the sodio derivative of the appropiate 2-oxo alkyl phosphonate to obtain the corresponding compound of formula III. The trans enone lactone is obtained stereospecifically. See D. H. Wadsworth et al. J. Org. Chem. 30, 680 (1965). For the Wittig reaction certain phosphonates are employed having the general formula:

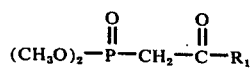

wherein $R_1$ has the meaning previously given. The phosphonates are prepared and used by methods known in the art. See Wadsworth et al., Corey et al., and Crabbé et al., references cited above. For this purpose as well as for the process of chart A above, the phosphonates are conveniently obtained by condensing the appropriate aliphatic acid ester with dimethyl methylphosphonate in the presence of n-butyllithium. For this purpose, acids of the general formula $R_1COOH$ are used in the form of their lower alkyl esters, preferably methyl or ethyl. For example methyl esters are formed from the acids by reaction with diazomethane. These aliphatic acids of various chain length, with or without branching and with or without substitution of 1 or 2-fluorine atoms within the scope of $R_1$ as defined above are known in the art or can be prepared by methods known in the art.

Aliphatic acids without branching are propionic, butyric, valeric, heptanoic, octanoic, nonanoic, decanoic, or undecanoic acids.

In the case of acids with branching, many are readily available, e.g., 2-methylpropionic, 2-methylbutyric, 2-ethylbutyric, 2,2-dimethylbutyric, 2-ethyl-2-methylbutyric, 2,2-diethylbutyric, 2-methylvaleric, 2-propylvaleric, 2,2-dimethylvaleric, 2-methyl-2-propylvaleric, 2-methylhexanoic, 2-ethylhexanoic, 2-butylhexanoic, 2,2-dimethylhexanoic, 2-butyl-2-methylhexanoic, 2-methylheptanoic, 2-propylheptanoic, 2-butylheptanoic, 2,2-diethylheptanoic, 2-methyl-2-propylheptanoic, 2-ethyloctanoic, 2-propyloctanoic, 2-ethyl-2-methyloctanoic, 2-ethylnonanoic, 2,2-dimethylnonanoic, and 2-methyldecanoic acid. Other acids are available by methods known in the art, for example reaction of a branched alkyl halide with sodium cyanide to form a nitrile and subsequent hydrolysis to the acid.

Many fluoro-substituted acids are readily available, e.g., 2-fluorobutyric, 2,2-difluorobutyric, 2-fluorovaleric, 2-fluorohexanoic, 2-fluoroheptanoic, 2-fluorooctanoic, 2-fluorononanoic, and 2-fluorodecanoic acids. Others are available by methods known in the art, for example by fluorination of 2-oxo aliphatic acids with sulfur tetrafluoride to give 2,2-difluoro acids. For reactions of $SF_4$ see Martin et al., J. Org. Chem. 27, 3164 (1962). For other syntheses of fluorinated acids see Henne et al., J. Am. Chem. Soc. 69, 281 (1947). For fluorination of a ketone function with $MoF_6 \cdot BF_3$ see Mathey et al., Tetrahedron 27, 2965 (1971). Other methods of synthesis include replacement of hydroxy by fluoro, see Ayer, U.S. Pat. No. 3,056,806; replacement of chloro or bromo by fluorine exchange with fluorides, or saturation of double bonds by fluorine atoms, see Advances in Fluorine Chemistry, M. Stacey et al., editors, Vol. 3, Butterworth and Co., 1963, especially pages 181–188.

Acids within the scope of the above formula wherein

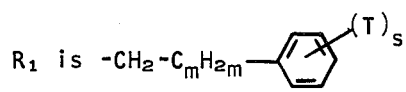

$R_1$ is $-CH_2-C_mH_{2m}-\langle\text{phenyl}\rangle(T)_s$ wherein $-C_nH_{2n}-$, T and s have the meanings given above, which can be used to prepare the desired phosphonates are:
methyl 2-phenylacetic
ethyl 2-(p-chlorophenyl)acetic
methyl 2-(o, p-dichlorophenyl)propionic
ethyl 2-phenylhexanoic
methyl 3-(p-chlorophenyl)propionic
ethyl 3-($\alpha,\alpha,\alpha$-trifluoro-p-tolyl)propionic
methyl 2-(m-methoxybenzyl)butyric
ethyl 4-phenylbutyric
ethyl 4-(p-chlorophenyl)butyric
methyl 4-(p-tolyl)butyric
methyl 4-(2-chloro-4-tolyl)butyric
methyl 5-phenylpentanoic
methyl 6-phenylhexanoic
methyl 7-phenylheptanoic
for example, methyl 2-phenylacetic yields dimethyl 2-oxo-3-phenylpropylphosphonate, ethyl 4-(p-chlorophenyl)butyric yields dimethyl 2-oxo-5-(p-chlorophenyl)pentylphosphonate, and the like.

Continuing with Chart I, the formula-IV compounds in which the $R_2$ substituent in E is hydrogen are obtained as a mixture of alpha and beta isomers by reduction of III. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, and when carbon-carbon double bond reduction is not a problem, the boranes, e.g., disiamylborane. The formula IV compounds in which the $R_2$ substituent in E is lower alkyl are obtained as a mixture of alpha and beta isomers by treating III with a lower-alkyl magnesium halide using conventional Grignard reaction methods. The alpha and beta isomers are separated by chromatography, e.g., silica gel chromatography or high pressure liquid chromatography. See, for example, "Modern Practice of Liquid Chromatography", J. J. Kirkland, ed., Wiley-Interscience, 1971.

The formula V compounds of Chart 1 are prepared by replacing the hydrogen of the hydroxyl group in the E substituent of the compounds of formula IV in which $R_2$ is hydrogen with a blocking group $R_5$ in the substituent $E_1$ of formula V. The function of this blocking group is to prevent attack of the hydroxyl group by subsequent reagents, especially the oxidizing reagent. It is a further requirement of this blocking group that it be replaceable by hydrogen at a later stage in the preparation of the prostaglandin-like products.

When the blocking group is silyl of the formula $-Si(G)_3$, the formula IV compound is transformed to a silyl derivative of formula V by procedures known in the art. See, for example, Pierce, "Silylation of Organic Compounds", Pierce Chemical Co., Rockford, Illinois (1968). The necessary silylating agents for these transformations are known in the art or are prepared by methods known in the art. See, for example, Post "Silicones and Other Organic Silicon Compounds", Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotriethylsilane, chlorotriisobutylsilane, chlorotriphenylsilane, chlorotris(p-chlorophenyl)silane, chlorotri-m-tolylsilane, and tribenzylchlorosilane. Alternatively the chlorosilane is used with the corresponding disilazanes. Examples of other silylating agents suitable for forming the formula V intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1,1-tetraphenylsilylamine.

When the blocking group is tetrahydropyranyl or tetrahydrofuranyl, the appropriate reagent, e.g., 2,3-dihydropyran or 2,3-dihydrofuran, is used in an inert solvent such as dichloromethane, in the presence of an acid condensing agent such as p-toluenesulfonic acid or pyridine hydrochloride. The reagent is used in excess, preferably 4 to 10 times theory. The reaction is carried out at about 20–50° C. When the blocking group is of the formula

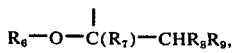

as defined above, the appropriate reagent is a vinyl ether, e.g., isobutyl vinyl ether or any vinyl ether of the formula $R_6—O—C(R_7)=CR_8R_9$ wherein $R_6$, $R_7$, $R_8$, and $R_9$ are as defined above; or an unsaturated cyclic or heterocyclic compound, e.g., 1-cyclohex-1-yl-methyl ether

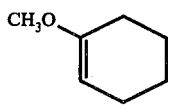

or 5,6-dihydro-4-methoxy-2H-pyran

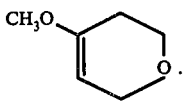

See C. B. Reese et al., J. Am. Chem. Soc. 89, 3366 (1967). The reaction conditions for such vinyl ethers and unsaturates are similar to those for dihydropyran above.

The Formula VI lactol (Chart I) is obtained on reduction of the protected formula V lactone using, for example, diisobutylaluminum hydride. The reduction is preferably carried out at about −60° to 70° C.

The formula VII compounds (Chart I) in which R is hydrogen are obtained from the lactols VI by the Wittig reaction using 4-carboxybutyltriphenylphosphonium bromide and sodium methylsulfinylmethide. The reaction is conveniently carried out at about 25° C. The phosphonium compound is known in the art and is readily available, e.g., by reaction of 4-bromo n-butryric acid with triphenylphosphine.

The free acids of formula VII (Chart I) (R is hydrogen) are converted to their corresponding esters (R is alkyl) by reacting the free acid with the appropriate diazohydrocarbon as hereinafter described.

The formula-VII compounds (Chart I) in which R is either hydrogen or alkyl as hereinbefore defined are oxidized at C-9 to give the corresponding compounds VIII. Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize one of the secondary hydroxy groups of the formula VII reactant is used. Acetone is a suitable diluent for this purpose. Reaction temperatures at least as low as about 0° C. should be used. Preferred reaction temperatures are in the range −10° to −50° C. An especially useful reagent for this purpose is methylsulfide-N-chlorosuccinimide in toluene. See E. J. Corey and C. U. Kim, J. Org. Chem. 38, 1233 (1973). Dichloromethane is a suitable diluent for this purpose. Reaction temperatures of below 30° C. should be used. Preferred reaction temperatures are in the range −50° to +10° C. The oxidation proceeds rapidly and is usually complete in about 1 to 2 hours. The formula VIII product thus obtained is isolated by conventional methods.

Examples of other oxidation reagents useful for this transformation are silver carbonate on Celite (Chem. Commun. 1102 (1969)), mixtures of chromium trioxide and pyridine J. Am. Chem. Soc. 75, 422 (1953), and Tetrahedron, 18, 1351 (1962)), t-butylchromate in pyridine (Biochem. J., 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965))).

Refer to Chart II, in the compounds of formula IV in which the $R_2$ substituent in E is lower-alkyl, it is not necessary to protect the hydroxy substituent with a blocking group. The compounds of formula IV in which the $R_2$ substituent in E is lower alkyl are those converted to the lactols of formula VI by reduction using for example, diisobutyl aluminum hydride. The reduction is preferably carried out at about −60° to −70° C.

The compounds of formula IXa are obtained from the lactols (VIa) by the Wittig reaction using 4-carboxybutyltriphenylphosphonium bromide and sodium methylsulfinyl methide as hereinbefore described for the conversion of the compounds of formula VI to the compounds of formula VII.

The free acids of formula IXa (Chart II) (R is hydrogen) are converted to their corresponding esters (R is alkyl) by reacting the free acid with, for example, the appropriate diazohydrocarbon as hereinafter disclosed.

The formula IXa compounds (Chart II) in which R is either hydrogen or alkyl as hereinbefore defined are oxidized at C-9 to give the corresponding compounds of formula Xa. The oxidation is carried out in the manner hereinbefore described for the oxidation of the compounds of formula VII to the compounds of formula VIII.

In the compounds of formula VII, VIII, IX, X, IXa and Xa when an ester form within the scope of the above definition of R is desired, the free acid is transformed to the desired ester by procedures known in the art. For example, esterification is readily accomplished by interaction of the free acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactant with the diazohydrocarbon be no longer than necessary to effect the desired esterification, preferably about one to about ten minutes, to avoid undesired molecular changes. diazohydrocarbons are known in the art or are prepared by methods known in the art. See, for example, Organic Reactions, John Wiley & Sons, Inc., New York, N.Y., Vol. 8, pp. 389–394 (1954).

Another more general prior art method for esterification of the novel PGC acids of this invention comprises slowly neutralizing the acid with slightly less than the stoichiometric amount of triethylamine, reacting the amine salt with p-toluenesulfonyl chloride, or isobutyl chloroformate, and then reacting the resulting mixed anhydride with an alcohol or phenol corresponding to the desired R moiety.

To obtain the compounds of formulas IX and X, the blocking groups on compounds VII and VIII are replaced with hydrogen, by hydrolysis in accordance with methods known in the art. Silyl groups are readily removed by prior art procedures known to be useful for transforming silyl ethers and silyl esters to alcohols and carboxylic acids, respectively. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary.

The formula IX, X, IXa and Xa compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the selected free acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula IX, X, IXa or Xa acid is dissolved in a suitable solvent of either moderate or low polarity. Examples of the former are ethanol, acetone, and ethyl acetate. Examples of the latter are ethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula IX, X, IXa or Xa acid with the stoichiometric amount of the corresponding quaternary ammonium hydroxide in water solution, followed by evaporation of the water.

DESCRIPTION OF THE PREFERRED EMBODIMENTS

The invention can be more fully understood by the following preparation and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass specrometer with a TO-4 source (ionization voltage 70 ev).

NMR spectra are recorded on a Varian A-60D spectrophotometer in deuterochloroform solutions with tetramethylsilane as an internal standard (downfield).

"Brine", herein, refers to an aqueous saturated sodium chloride solution.

The abbreviation THP means "tetrahydropyranyl".

The intermediate and final products of this application are numbered in accordance with the prostanoic acid numbering system hereintofore described, including the intermediates even when the acid side chain is not present.

Preparation I 5-formyl-2-hydroxy-4-cyclopentene-1-acetic acid γ-lactone, unsaturated aldehyde II (refer to Chart III)

A 3.6 l. quantity of methylene chloride and 172 g. of pyridine is cooled to 10° C. while stirring under a nitrogen atmosphere. To this solution is added, in four portions, 108 g. of chromium trioxide (dried over phosphorous pentoxide) over about 20 minutes. The dark brown mixture is held at about 15° C. for 15 minutes after the addition and then warmed to 20° C. over a period of about 40 minutes. The pyridine-chromium trioxide complex thus obtained is then treated rapidly with 1 l. of methylene chloride containing 50 g. (0.18 mole) of 2-hydroxy-4-benzoxy-5-hydroxymethylcyclopentaneacetic acid γ-lactone (XI) disclosed in copending application Ser. No. 127,347, filed Mar. 23, 1971. The reaction is monitored by TLC on silica gel plates developed with ethyl acetate. In this system the benzoate alcohol (XI) had an Rf of 0.53, the (2-hydroxy-4-benzoxy-5-formyl cyclopentaneacetic acid γ-lactone (XII) an Rf of 0.79, and the unsaturated aldehyde (II) 0.72. After 118 hours the elimination of the benzoate from (XII) is found to be complete. The reaction mixture is then filtered through a bed of Celite. The residues are washed with methylene chloride. The combined methylene chloride solution is washed with N-hydrochloric acid and 5% sodium bicarbonate. After drying over sodium sulfate the methylene chloride is distilled. The residue is chromatographed over 2 kg. of silica gel, eluting with (80–20) ethyl acetate-cyclohexane. The progress of the column is monitored by TLC. The fractions containing product are combined and distilled leaving 12.95 g. (47% yield) of light yellow crystals. Two recrystallizations from ethyl acetate-cyclohexane gives very pale yellow crystals of the unsaturated aldehyde II, m.p. 75°–76.5° C; infrared spectral absorptions at 3050, 2740w, 1775, 1670, 1615, 1385, 1190, 1175, 1050, 1025, 1020, 960, 935 and 730 cm$^{-1}$; $\lambda_{max}^{ETOH}$: 229mμ (11,750) and 317mμ (40); NMR (CDCl$_3$): peaks at 2.7–3.2, 3.5–4.0, 5.1–5.4, 6.85–7.05 and 9.60δ.

EXAMPLE I 2-hydroxy-5-(3-oxo-trans-1-octenyl)-4-cyclopenten-1- acetic acid, γ-lactone, the unsaturated Ketone III (refer to Chart I) wherein

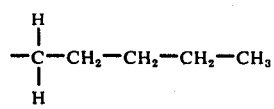

A 460 ml, quantity of tetrahydrofuran (dried by passing through a comumn of 13X molecular sieve and neutral alumina) and 3.2 g. of 50% sodium hydride dispersed in oil is cooled to about 5° C. while stirring under a nitrogen atmosphere. The mixture is treated with 14.64 g. of dimethyl-2-oxoheptyl phosphonate and the mixture allowed to warm to room temperature. After about 2 hours the mixture is cooled to about 0° C. and treated with 5 g. of unsaturated aldehyde (II) dissolved in 30 ml. of benzene. The reaction mixture is allowed to warm to room temperature and stirred for about 1.5 hours. The reaction mixture is then treated with 6 ml. of acetic acid and the solvent evaporated in vacuo. The residue thus obtained is partitioned between ethyl acetate and saturated brine. The ethyl acetate solution is dried over magnesium sulfate and evaporated in vacuo. The residue thus obtained is chromatographed over 1 kg. of silica gel, eluting with (50—50) ethyl acetate-Skellysolve B hexanes. Five hundred ml. fractions are collected. The fractions which are found to contain the desired product by TLC are combined and evaporated leaving 5.08 g. (62% yield) of crystalline unsaturated ketone (III). Three recrystallizations from cyclohexane gives nearly colorless crystals of unsaturated ketone (III) m.p. 80°-83° C; infrared (mull) spectral absorption at 1760, 1690, 1615, 1590, 1320, 1175, 1080, 1045, 1020, 985 and 925 cm$^{-1}$; $\lambda_{max}^{ETOH}$: 276mμ (21,200): NMR (CDCl$_3$) peaks at 3.5–4.0, 5.1–5.5, 5.85–6.4 and 7.1–7.65δ.

Following the procedure of Example I but replacing the dimethyl 2-oxoheptylphosphonate with the various phosphonates within the scope of the formula $$(CH_3)_2 \overset{O}{\overset{\|}{P}} CH_2 \overset{O}{\overset{\|}{C}} R_1 ;$$

responding compounds of formula III (Chart I) are obtained. For example, the following conversions are representative;

1. dimethyl 2-oxo-3-methylheptyl phosphonate to the optically active compound of formula III wherein R$_1$ is

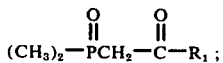

2. dimethyl 2-oxo-3,3-dimethylheptyl phosphonate to the optically active compound of formula III wherein R$_1$ is

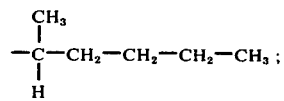

3. dimethyl 2-oxo-3-fluoroheptyl phosphonate to the optically active compound of formula III wherein R$_1$ is

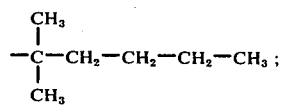

4. dimethyl 2-oxo-3,3-difluoroheptyl phosphonate to the optically active compound of formula III wherein R$_1$ is

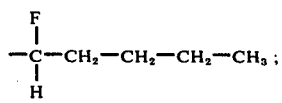

5. dimethyl 2-oxobutyl-4-phenyl phosphonate to the optically active compound of formula III wherein R$_1$ is

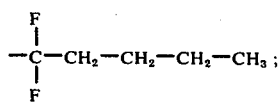

6. dimethyl 2-oxobutyl-4-(p-chlorophenyl) phosphonate to the optically active compound of formula III wherein R$_1$ is

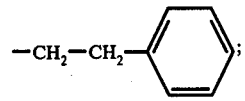

7. dimethyl 2-oxobutyl-4-(o-methylphenyl) phosphonate to the optically active compound of formula III wherein R$_1$ is

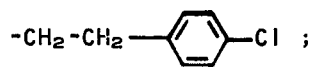

EXAMPLE 2

2-hydroxy-5-[(3s)-3-hydroxy-trans-1-ocetnyl]-4-cyclopenten-1-acetic acid, γ-lactone (IV) and 2-hydroxy-5-[(3R)-3-hydroxy-trans-1-octenyl]-4-cyclopenten-1-acetic acid, γ-lactone (IV), the 15α Alcohol (IV) and the 15β Alcohol (IV), respectively, (refer to Chart I) the optically active compounds of formula IV wherein R$_1$ is

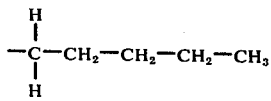

and E in the 15α-alcohol is

and E in the 15β alcohol is

A 7.57-g. quantity of unsaturated ketone III (refer to Chart I) wherein R$_1$ is

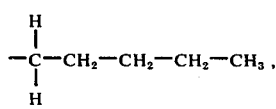

is dissolved in 150 ml. of absolute ethanol and the resultant solution stirred at about 25° C. under a nitrogen atmosphere. To the solution is added, over about 1 hour, 1 g. of sodium borohydride. After about 1.5 hours, 20 ml. of 1 molar phosphate buffer (pH 6.5) is added. The ethanol mixture is evaporated in vacuo and the residue partitioned between methylene chloride and 60 ml. 1N HCl. The methylene chloride layer is dried over sodium sulfate and distilled in vacuo giving 6.74 g. of oil which is chromatographed over 650 g. of silica gel, eluting with (40–60) ethyl acetate-Skellysolve B hexanes. 250 ml. fractions are collected. The fractions which are found by TLC to contain the less polar alcohol are combined to give 1.66 g. of the corresponding 15α-alcohol (IV). The fractions which are found to contain the more polar alcohol by TLC are combined to give 0.572 g. of the corresponding 15β alcohol (IV). The intermediate fractions give a mixture of the 15α and 15β alcohols (IV); the 15α-alcohol (IV) shows infrared spectra absorption at: 3430, 1765, 1625w sh, 1355, 1295, 1180, 1070, 1030, and 975 cm$^{-1}$; $\lambda_{max}^{ETOH}$ 229sh m$\mu$ (9,400), 234 m$\mu$ (10,300), 242sh m$\mu$ (7,700), 268sh m$\mu$ (1,000), and high resolution mass spectrum: mol. wt. 250.1551; the 15β-alcohol (IV) shows infrared absorption at 3430, 1765, 1625sh, 1355, 1290, 1180, 1070, 1025 and 975 cm$^{-1}$; $\lambda_{max}^{ETOH}$ 228sh m$\mu$ (10,100), 234m$\mu$ (11,000), 242sh m$\mu$ (7,850) and 268sh m$\mu$ (626); and high resolution mass spectrum: mol. wt. 250.1555.

Following the procedure of Example 2 other compounds of formula III are likewise reduced to the corresponding 15α and 15β-alcohols of formula IV. For example, the compounds prepared and listed under 1–7 in Example 1, above, are used to produce, respectively, the following optically active compounds of formula IV 1. the 15α and 15β alcohols of formula IV wherein E is

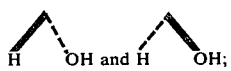

and R$_1$ is

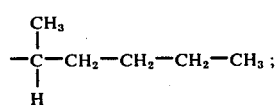

2. the 15α and 15β alcohols of formula IV wherein is

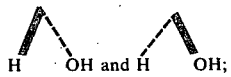

in and R$_1$ is

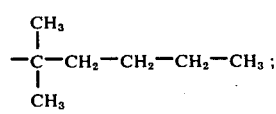

3. the 15α and 15β alcohols of formula IV wherein E is

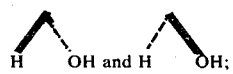

and R$_1$ is

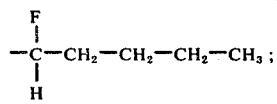

4. the 15α and 15β alcohols of formula IV wherein E is

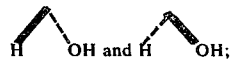

and R$_1$ is

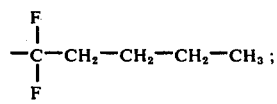

5. the 15α and 15β alcohols of formula IV wherein is

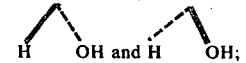

and R$_1$ is

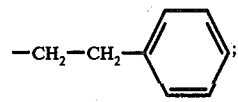

6. the 15α and 15β alcohols of formula IV wherein is

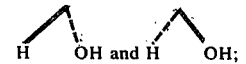

and R$_1$ is

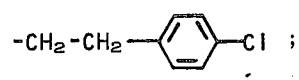

7. the 15α and 15β alcohols of formula IV wherein E is

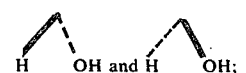

and R$_1$ is

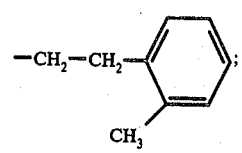

EXAMPLE 3

2-hydroxy-5-[(3S)-3-hydroxy-3-methyl-trans-1-octenyl]-4-cyclopenten-1-acetic acid, γ-lactone (IV) and
2-hydroxy-5[(3R)-3-hydroxy-3-methyl-trans-1-octenyl]-4-cyclopenten-1-acetic acid, γ-lactone (IV), the 15-S and the 15R-alcohols IV, (refer to Chart I) the optically active compounds of formula IV, wherein E is

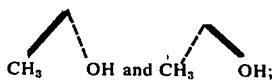

and $R_1$ is

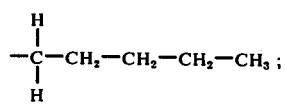

Refer to Chart I. A solution of 0.2 g. of the formula III 15-oxo compound wherein $R_1$ has the meaning given in the title immediately, above, in 15 ml. of tetrahydrofuran is treated, with stirring at −78° C., with 3M methyl magnesium bromide in ether, added dropwise. After about 2 hr. there is added dropwise to the mixture at −78° C. 10 ml. of saturated aqueous ammonium chloride. The mixture is warmed to 25° C. and diluted with diethyl ether and water. The organic phase is washed with brine, dried and concentrated to give a mixture of the 15S and 15R formula-IV alcohols.

Following the procedure of Example 3 other 15-oxo compounds of formula III are likewise converted to the corresponding 15S and 15R-methyl compounds of formula IV. For example thosse prepared and listed under 1–7 in Example 1, above, are used to produce, respectively, the compounds corresponding to those listed under 1–7 of Example 2, above, with a 15α- and 15β-methyl substituents present in place of hydrogen.

In the same manner the other 15-alkyl compounds of formula IV are prepared from the corresponding 15-oxo compounds of formula III by substituting the appropriate alkyl magnesium bromide in place of methyl magnesium bromide for example, ethyl magnesium bromide, propyl magnesium bromide, butyl magnesium bromide and the like.

EXAMPLE 4

2-hydroxy-5-[(3S)-3-(tetrahydro-2-H-pyran-2-yl)oxy]-trans-1-octenyl-4-cyclopenten-1-acetic acid, γ-lactone, the tetrahydropyranyl ether V (refer to Chart K) wherein $E_1$ is

and $R_1$ is

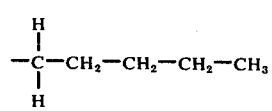

Refer to Chart I. The 15α-alcohol (0.92 g.) prepared in Example 2, above, the compound of formula IV wherein E is

and $R_1$ has the meaning given in the title immediately, above, is dissolved in 20 ml. of methylene chloride. The solution is treated with 3 g. of dihydropyran and 0.1 g. of pyridine hydrochloride. TLC shows the reaction to be finished after about 6 hours. The reaction is then percolated through a bed of silica gel. The product is rinsed free of the silica with ethyl acetate. Distillation of the solvent in vacuo gives 1.46 g. of the product which is used as such for the next step, having NMR (CDCl$_3$) peaks at 0.88, 1.35, 1.62, 5.63, 6.18 and 6.46δ.

Following the procedure of Example 4, above, other of the compounds represented by formula IV wherein the $R_2$ substituent in E is hydrogen are likewise converted to the corresponding tetrahydropyranyl derivatives, for example those listed under 1–7 in Examples 2 and 3, above.

Similarly, other blocking groups are used in place of the tetrahydropyranyl in accordance with methods known in the art and disclosed hereinabove.

EXAMPLE 5

9α-hydroxy-15(S)-[tetrahydro-2H-pyran-2-yl)oxy]-5-cis-11,13-trans-prostatrienoic acid, the compound of formula VII (refer to Chart I) wherein R is hydrogen; $E_1$ is

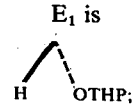

and $R_1$ is

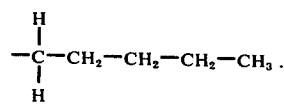

The tetrahydropyranyl lactone (1.46 g.) prepared in Example 4, above, the compound of formula V wherein $E_1$ and $R_1$ have the meanings given in the title immediately, above, is dissolved in 18 ml. of toluene and the resultant solution cooled in a Dry Ice-methanol bath while stirring under a nitrogen atmosphere. To this is added over about 30 minutes 1.4 ml. of diisobutyl aluminum hydride in 14 ml. of toluene. Thirty minutes after the completion of the addition, 5.6 ml. of tetrahydrofuran and 2.8 ml. of water are added dropwise. After warming to room temperature and stirring for about 3 hours, the precipitated aluminum salts are removed by filtration. The solids are washed with benzene. The filtrates are combined and washed with brine and dried over sodium sulfate. Distillation of the benzene gives 1.22 g. of corresponding lactol (VI).

In a separate reactor, 3 ml. of dimethyl sulfoxide (dried over 13X molecular sieve and neutral aumina) is treated with 0.58 g. of 50% sodium hydride dispersed in oil. The mixture is heated to 65°–70° C. for about 1.25 hours. The reaction is then cooled to 15°–20° C. and 2.7 g. of 4-carboxybutyltriphenylphosphonium bromide in 5 ml. of dry dimethyl sulfoxide is added over about 10 minutes. Fifteen minutes after the addition of the phosphonium salt, the reaction is treated with 0.490 g. of the above lactol (VI) in 3 ml. of dry dimethyl sulfoxide. After about 3.5 hours the reaction is treated with 40 ml. of benzene, cooled to 15° C., and then treated with 2 g. of sodium bisulfate in 17 ml. of water. The layers are separated and the benzene layer is extracted with water. After drying over sodium sulfate the benzene solution is distilled in vacuo to give the free acid (VII) which is purified in accordance with known methods, for example, chromatography, having NMR ($CDCl_3$) peaks at 0.87, 1.35, 1.65, 2.22, 2.32, 4.75, 5.62, 6.15 and 6.42δ.

Following the procedure of Example 5 but replacing the starting lactone with other compounds of formula V for example, the tetrahydropyranyl blocked compounds prepared in Example 4, above; the following are produced:

1. the optically active compound of formula VII wherein $E_1$ is

and $R_1$ is

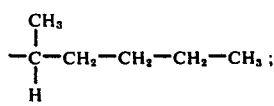

2. the optically active compound of formula VII wherein $E_1$ is

and $R_1$ is

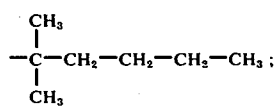

3. the optically active compound of formula VII wherein $E_1$ is

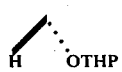

and $R_1$ is

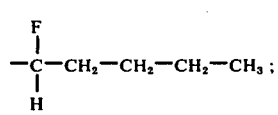

4. the optically active compound of formula VII wherein $E_1$ is

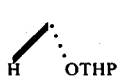

and $R_1$ is

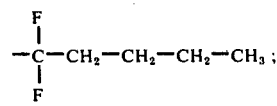

5. the optically active compound of formula VII wherein $E_1$ is

and $R_1$ is

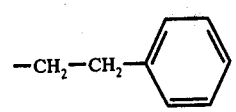

6. the optically active compound of formula VII wherein $E_1$ is

and $R_1$ is

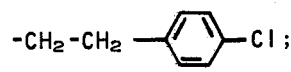

7. the optically active compound of formula VII wherein $E_1$ is

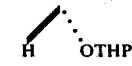

and $R_1$ is

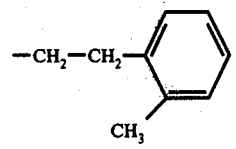

In the same manner the corresponding 15-lower alkyl compounds of formula IXa (Chart II) for example, those in which E is

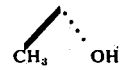

are likewise prepared from the corresponding 15-lower-alkyl compounds of formula IV, wherein the $R_2$ substituent in E is lower alkyl, for example, the optically active compound of formula IXa wherein R is hydrogen, $E_3$ is

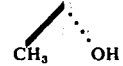

and $R_1$ is

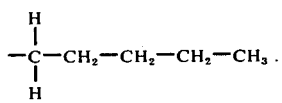

EXAMPLE 6

[methyl 9α-hydroxy-15(S)-[tetrahydro-2H-pyran-2-yl)oxy]-5-cis-11,13-trans-prostatrienoate] (VII), the optically active compound of formula VII (refer to Chart I) wherein R is methyl; $E_1$ is

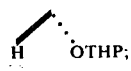

and $R_1$ is

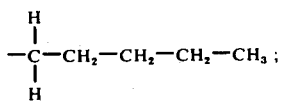

The free acid prepared in Example 5, above, is dissolved in ca 5 ml. of tetrahydrofuran and treated with an ethereal solution of diazomethane. The resultant solution is then distilled in vacuo and the residue chromatographed over 100 g. of silica gel. The column is eluted with (30–70) ethyl acetate-cyclohexane, collecting 40 ml. fractions. The fractions which are shown by TLC to contain the desired product are combined to give 0.258 g. of the corresponding methyl ester (VII) having NMR ($CDcl_3$) peaks at 0.88, 1.27, 1.65, 2.33, 3.65, 6.10 and 6.35δ.

Following the procedure of Example 6, other compounds of formula VII (Chart I) and (IX)a (Chart II), wherein R is hydrogen are likewise converted to the corresponding compounds of formula VII and IXa, respectively, wherein R is methyl, for example, those free acids listed in Example 5, above, are converted to the corresponding compounds wherein R is methyl.

In the same manner other alkyl esters of formula VII and IXa are likewise prepared from the corresponding free alcohols by substituting the selected diazoalkane in place of diazomethane.

EXAMPLE 7

[methyl-9-oxo-15(S)-[(tetrahydro-2H-pyran-2-yl)oxy]-5-cis-11,13-trans-prostatrienoate] (VIII), the tetrahydropyranyl ether of $PGC_2$ methyl ester, the optically active compound of formula VIII (refer to Chart I), wherein R is methyl; $E_1$ is

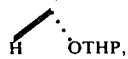

and $R_1$ is

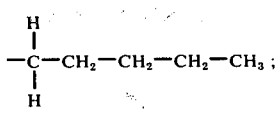

The hydroxytetrahydropyranyl methyl ester (223 mg.) prepared in Example 6 is dissolved in 6 ml. of acetone. The resultant solution is cooled to −20° C. and treated over a period of about 6 minutes with 0.2 ml. of 2.67 M chromium trioxide (Jones reagent: 30 ml. $H_2O$, 8.7 ml. $H_2SO_4$ and 10.3 g. $CrO_3$). After about 15 minutes the reaction mixture is then treated with 0.3 ml. isopropyl alcohol and stirred an additional 15 minutes at −20° C. The reaction mixture is then diluted with water and extracted with metylene chloride. The methylene chloride is extracted with saturated sodium chloride solution, dried over magnesium sulfate and distilled in vacuo to give 214 mg. of residue containing the desired compound of formula VIII wherein R, E and $R_1$ have the meanings given in the title immediately above, UV ($Et_2O$) peak at 234 nm.

Following the procedure of Example 6, above, other compounds of formula VII (refer to Chart I) and the compounds of formula IXa (refer to Chart II) are likewise oxidized to the corresponding compounds of formula VIII, and Xa, respectively, for example those compounds of formula VII and IXa prepared and listed in Examples 5 and 6, above, to give the corresponding 9-oxo compounds of formula VIII and IXa, respectively, for example:

1. the optically active compounds of formula VIII, wherein R is hydrogen; $E_1$ is

and $R_1$ is

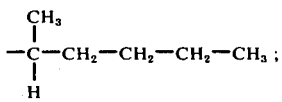

2. the optically active compound of formula VIII, wherein R is hydrogen; $E_1$ is

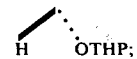

and $R_1$ is

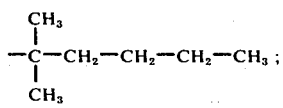

3. the optically active compound of formula VIII, wherein R is hydrogen; $E_1$ is

and $R_1$ is

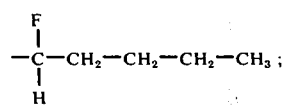

4. the optically active compound of formula VIII, wherein R is hydrogen; $E_1$ is

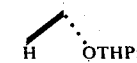

and R₁ is

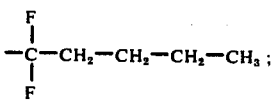

5. the optically active compound of formula VIII, wherein R is hydrogen; E₁ is

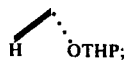

and R₁ is

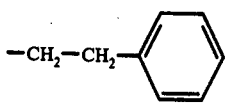

6. the optically active compound of formula VIII, wherein R is hydrogen; E₁ is

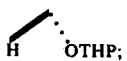

and R₁ is

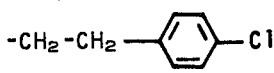

7. the optically active compound of formula VIII, wherein R is hydrogen; E₁ is

and R₁ is

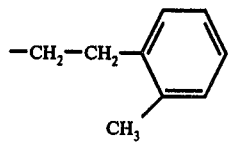

8. 15(S)-15-methyl PGC₂, the optically active compound of formula XIa, wherein R is hydrogen; E₁ is

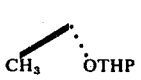

and R₁ is

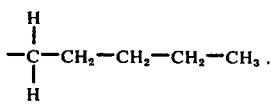

EXAMPLE 8

PGC₂ methyl ester [methyl 9-oxo-15(S)-hydroxy-5-cis, 11,13-trans-prostatrienoate], the compound of formula VIII wherein R is methyl; E₁ is

and R₁ is

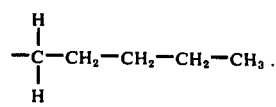

The 214 mg. of residue prepared in Example 7 above, is dissolved in acetic acid-water-tetrahydrofuran (4.5–2.25–0.75 ml.) and the solution stirred under nitrogen at 40° C. for 2.5 hours. The reaction is then quenched with ice and 0.5 M phosphate buffer (pH 6.5). The aqueous mixture is extracted with ether. The ether is extracted 3X with 0.5 M phosphate buffer (pH 6.5) and dried over magnesium sulfate. Distillation of the solvent in vacuo leaves 139 mg. of oil which is chromatographed over 20 g. of acid washed silica gel, eluting with (30–20) ethyl acetate-cyclohexane. Five ml. fractions are collected.

The fractions which are determined by TLC to contain the desired product are combined to give 40 mg. of PGC₂ methyl ester; I.R. (CH₂Cl2) spectral absorptions at 2900, 2810, 1720, 1450w, 1380, 1240, 1045 cm⁻¹, UV (ET₂O): 229sh, 234mμ; NM (CDCl₃) peaks at 3.97–4.38, 5.10–5.50, 5.7 and 6.3 δ; high resolution mass spectrum observed 348.2285 and low resolution mass spectrum at 41, 43, 55, 67, 71, 79, 81, 99, 109 and 217 atomic mass units.

Following the procedure of Example 8, above, other tetrahydropyranyl ethers of formulas VII and VIII are likewise hydrolyzed to the corresponding compounds of formula IX and X repsectively, to obtain, for example, 1. 16-methyl PGC₂, the compound of formula X wherein E is

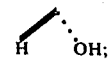

R is hydrogen; and R₁ is

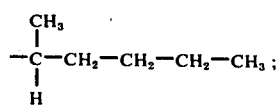

2. 16, 16-dimethyl PGC₂, the compound of formula X wherein E is

R is hydrogen; and R₁ is

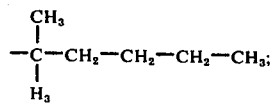

3. 16-fluoro PGC₂, the compound of formula X wherein E is

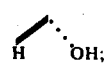

R is hydrogen; and $R_1$ is $$-\underset{H}{\overset{F}{C}}-CH_2-CH_2-CH_2-CH_3;$$

4. 16,16-difluoro $PGC_2$, the compound of formula X wherein E is

H͗ ͐OH;

R is hydrogen and $R_1$ is $$-\underset{F}{\overset{F}{C}}-CH_2-CH_2-CH_2-CH_3;$$

5. the $PGC_2$ analog of formula X wherein, E is

H͗ ͐OH,

R is hydrogen; and $R_1$ is $-CH_2-CH_2-\langle\text{phenyl}\rangle$ 6. the $PGC_2$ analog of formula X wherein, E is

H͗ ͐OH,

R is hydrogen; and $R_1$ is $-CH_2-CH_2-\langle\text{phenyl}\rangle-Cl;$ 7. the $PGC_2$ analog of formula X wherein, E is

H͗ ͐OH,

R is hydrogen; and $R_1$ is $-CH_2-CH_2-\langle\text{phenyl with }CH_3\rangle$ and the corresponding alkyl esters of the compounds listed under 1–7, above, can likewise be prepared by starting with the corresponding compound of formula VIII, wherein R is alkyl, for example, methyl.

In the same manner following the procedure of Example 8 the protective 15-tetrahydropyranyl groups are likewise hydrolyzed from the 9α-hydroxy compounds of formula VII, to obtain the 15-free hydroxy compounds of formula IX. Thus, those corresponding otherwise to the $PGC_2$ compounds listed under 1–8, in the immediately proceeding paragraph are used to obtain for example, methyl 9α,15(S)-dihydroxy-5-cis-11,13-trans-prostatrienoate, a compound of formula IX wherein R is methyl; E is

H͗ ͐OH;

and $R_1$ is $$-\underset{H}{\overset{H}{C}}-CH_2-CH_2-CH_2-CH_3.$$

EXAMPLE 9

$PGC_2$ Sodium Salt
[9-oxo-15(S)-hydroxy-5-cis-11,13-trans-prostatrienoic acid sodium salt] (X)

A solution of $PGC_2$ (X) (9-oxo-15(S)-hydroxy-5-cis-11,13-trans-prostatrienoic acid)(100 mg.) in 50 ml. of a water-ethanol mixture (1:1) is cooled to 5° C. and neutralized with an equivalent amount of 0.1 aqueous sodium hydroxide solution. The neutral solution is freeze dried to give $PGC_2$ sodium salt.

Following the procedure of Example 9 but using potassium hydroxide, calcium hydroxide, tetramethylammonium hydroxide, and benzyltrimethylammonium hydroxide in place of sodium hydroxide, there are obtained the corresponding salts of $PGC_2$.

Also following the procedure of Example 9 the $PGC_2$ type compounds of formula IX, X, IX$a$ and X$a$ are transformed to the sodium, potassium, calcium, tetramethylammonium, and benzyltrimethylammonium salts.

I claim:

1. An optically active compound of the formula:

[Structure: cyclopentenone with COOR side chain and $CH_2-C_mH_{2m}-\langle\text{phenyl}\rangle-(T)_s$ side chain, with $E_2$]

or a racemic compound of that formula and the mirror image thereof, wherein R is hydrogen, alkyl of 1 to 12 carbon atoms, inclusive, cycloalkyl of 3 to 10 carbon atoms, inclusive, phenyl, aralkyl of 7 to 12 carbon atoms, inclusive, phenyl substituted with 1 to 3 chlorine atoms, inclusive, or phenyl substituted with lower-alkyl of 1 to 4 carbon atoms inclusive; $E_2$ is H͗ ͐OH or H͗ ͐OH;

—$C_mH_{2m}$— is a valence bond or alkylene of 1 to 9 carbon atoms, inclusive, with 1 to 6 carbon atoms, inclusive, in a chain between —CH$_2$— and the ring; T is lower-alkyl of 1 to 4 carbon atoms, inclusive, fluoro, chloro, trifluoromethyl or —OR$_2$ in which R$_2$ is hydrogen or lower-alkyl of 1 to 4 carbon atoms, inclusive; and s is 0 to 3 inclusive, with the proviso that not more than two T's are other than alkyl.

2. An optically active compound according to claim 1, wherein E$_2$ is

and R is alkyl of 1 to 4 carbon atoms inclusive.

3. A compound according to claim 2, wherein —C$_m$H$_{2m}$— is methylene.

4. A compound according to claim 3, wherein s is 0.

5. An optically active compound of the formula:

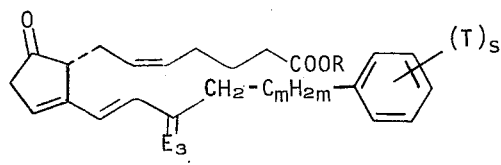

or a racemic compound of that formula and the mirror image thereof, wherein R is hydrogen, alkyl of one to 12 carbon atoms, inclusive, cycloalkyl of 3 to 10 carbon atoms, inclusive, phenyl, aralkyl of 7 to 12 carbon atoms, inclusive, phenyl substituted with one to 3 chlorine atoms, inclusive, or phenyl substituted with lower alkyl of one to 4 carbon atoms, inclusive; —C$_m$H$_{2m}$— is a valence bond or alkylene of one to 9 carbon atoms, inclusive, with one to 6 carbon atoms, inclusive, in the chain between the —CH$_2$— and phenyl ring; and T is lower alkyl of one to 4 carbon atoms, inclusive, fluoro, chloro, trifluoromethyl, or —OR$_2$, in which R$_2$ is hydrogen or lower alkyl of one to 4 carbon atoms, inclusive, and s is zero to 3, inclusive, with the proviso that not more than two T's are other than alkyl; and E$_3$ is

or

in which R$_{12}$ is lower alkyl of one to 4 carbon atoms, inclusive.

6. An optically active compound according to claim 5, wherein R is hydrogen or alkyl of one to 4 carbon atoms, inclusive; and E$_3$ is

in which R$_{12}$ is methyl or ethyl.

7. A compound according to claim 6 wherein s is zero.

8. An optically active compound of the formula

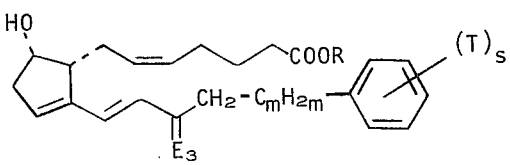

or a racemic compound of that formula and the mirror image thereof, wherein R is hydrogen, alkyl of one to 12 carbon atoms, inclusive, cycloalkyl of 3 to 10 carbon atoms, inclusive, phenyl, aralkyl of 7 to 12 carbon atoms, inclusive, phenyl substituted with one to 3 chlorine atoms, inclusive, or phenyl substituted with lower alkyl of one to 4 carbon atoms, inclusive; —C$_m$H$_{2m}$— is a valence bond or alkylene of one to 9 carbon atoms, inclusive, with one to 6 carbon atoms, inclusive, in the chain between the —CH$_2$— and phenyl ring; wherein E is

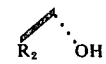

or

in which R$_2$ is hydrogen or lower alkyl of one to 4 carbon atoms, inclusive.

9. A compound according to claim 8, wherein R is hydrogen or alkyl of one to 4 carbon atoms, inclusive, and E is

10. A compound according to claim 9, wherein s is zero.

11. A compound according to claim 8, wherein R is hydrogen or alkyl of one to 4 carbon atoms, inclusive, and E is

wherein R$_2$ is methyl or ethyl.

12. A compound according to claim 11, wherein s is zero.

* * * * *

UNITED STATES PATENT AND TRADEMARK OFFICE
CERTIFICATE OF CORRECTION

PATENT NO. : 3,993,686
DATED : November 23, 1976
INVENTOR(S) : Robert C. Kelly

It is certified that error appears in the above-identified patent and that said Letters Patent are hereby corrected as shown below:

The title should read -- PHENYL SUBSTITUTED PROSTAGLDIN-C-TYPE ANALOGS --;

Column 3, line 62, "1 4" should read -- 1 to 4 --;
Column 5, line 6, "inclusive," should read -- inclusive, $E_2$ is --;
Column 7, line 30, "and or the" should read -- and on the --;
Column 19, line 2, "wherein" should read -- wherein $R_1$ is --;
Column 32, lines 65-69, " 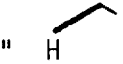 or 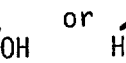 ;" should read -- 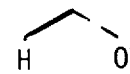 or 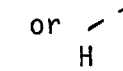 ;--

𝕊igned and 𝕊ealed this

Seventh Day of March 1978

[SEAL]

Attest:

RUTH C. MASON
Attesting Officer

LUTRELLE F. PARKER
Acting Commissioner of Patents and Trademarks